ively. Brown, J.R. (1995). "The 1995 National Association of Academic Administrators".

United States Patent [19]
Yashima

[11] Patent Number: 4,748,975
[45] Date of Patent: Jun. 7, 1988

[54] SUPPORTER

[76] Inventor: Seiichi Yashima, 186, Tamaboko 3-chome, Kanazawa-shi, Ishikawa-ken, 921, Japan

[21] Appl. No.: 89,569

[22] Filed: Aug. 26, 1987

[30] Foreign Application Priority Data

Aug. 27, 1986 [JP] Japan ............................ 61-200794

[51] Int. Cl.$^4$ ............................................. A61F 13/00
[52] U.S. Cl. ................................................... 128/155
[58] Field of Search ................... 128/155, 77, 78, 80 C

[56] References Cited

U.S. PATENT DOCUMENTS

| | | | |
|---|---|---|---|
| 4,085,752 | 4/1978 | Canale | 128/155 |
| 4,671,267 | 6/1987 | Stout | 128/155 |
| 4,702,237 | 10/1987 | Gianopoulos | 128/155 |
| 4,706,662 | 11/1987 | Thompson | 128/155 |

*Primary Examiner*—Gregory E. McNeill
*Attorney, Agent, or Firm*—Oblon, Fisher, Spivak, McClelland & Maier

[57] ABSTRACT

A supporter which can be attached simply to a portion of the body without the necessity of operation of attaching the same from the side of an end of a limb and irrespective of the thickness of the portion to which the supporter is to be attached and which can be attached to the shoulder, the ankle, the knee, a hand root portion, or the elbow to which it is difficult to attach a supporter due to the presence of a projection. The supporter comprises a supporter body formed in an elliptical shape and having a longitudinal slit formed at a central portion thereof. The supporter body is divided at a longitudinal end portion thereof by another longitudinal slit to form a pair of fastening ends, and a face fastener is secured to a human body non-contacting face of the supporter body and also to an opposite face of an end portion of each of the fastening ends of the supporter.

7 Claims, 4 Drawing Sheets

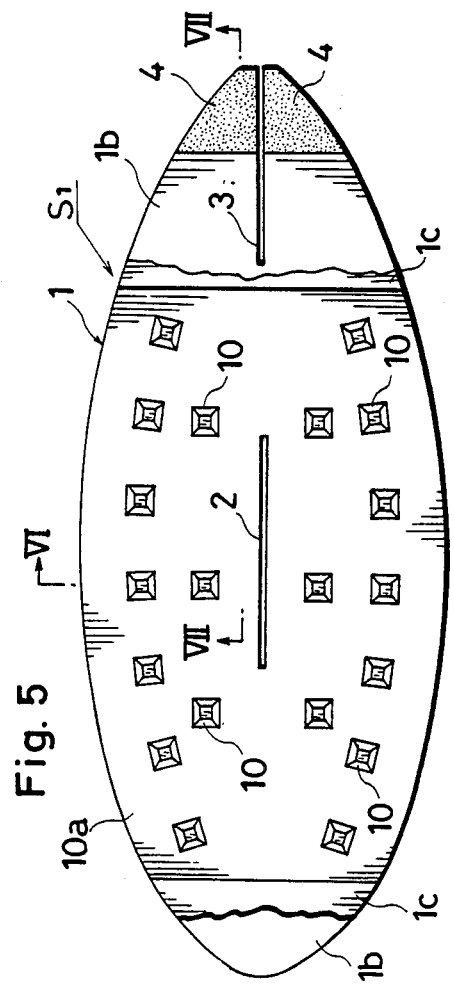
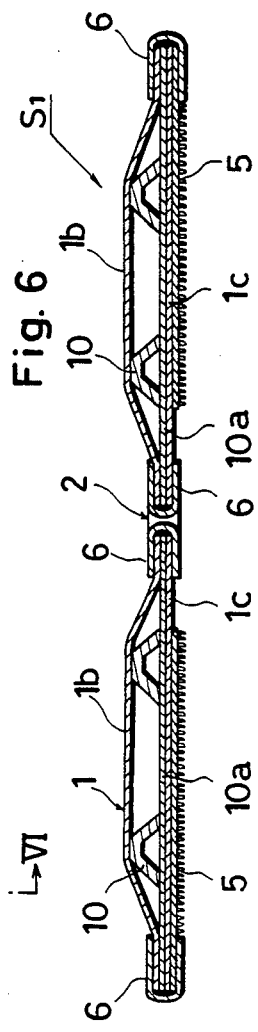
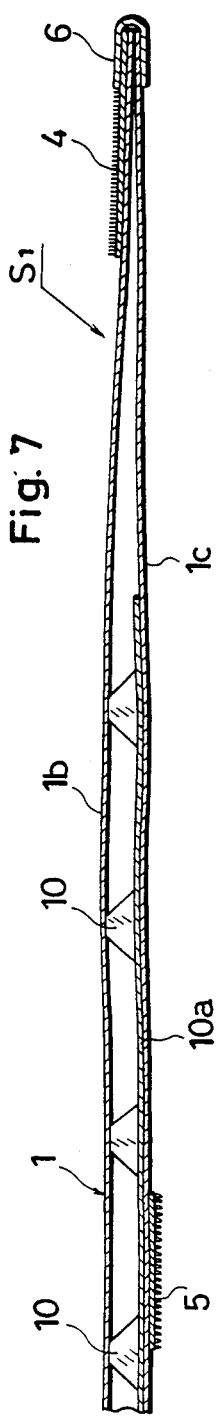

SUPPORTER

BACKGROUND OF THE INVENTION

1. Field of the Invention

This invention relates to a supporter which is used to bind a portion of the human body.

2. Prior Art

A supporter is widely used as a device for binding a portion of the human body for its fixation in order to treat an injured person. Conventional supporters employ a stretch fabric such as a knit fabric with a rib stitch part having a tubular configuration in accordance with the thickness of a portion of the body to bind therewith.

However, since such conventional supporters have a simple tubular configuration, various kinds of supporters of different sizes must be prepared for various thicknesses of portions of the body to be used for. Besides, when a supporter is to be attached to a portion of a limb such as the elbow or the knee which is remote from an end of the limb, operation is required to first fit the tubular supporter onto the limb from the end of the limb and then draw it up to a portion to which it is to be actually attached. Such operation is complicated and troublesome. Moreover, such conventional supporters have another drawback that, since they have a tubular configuration, it is impossible to attach a conventional supporter to the shoulder, the ankle or a portion of the hand from the wrist to the palm (hereinafter referred to as hand root portion) at which a projection is present.

SUMMARY OF THE INVENTION

Accordingly, it is an object of the present invention to provide a supporter which can be attached simply to a portion of the human body irrespective of the thickness of the human body portion and whether or not there is a projection such as a thumb present at or around the human body portion.

According to the present invention, a supporter is characterized in that a supporter body formed in an elliptical shape has a slit formed in a direction of a longitudinal axis at a central portion thereof and is divided at one of opposite longitudinal end portions thereof by another slit extending in the direction of the longitudinal axis of the supporter body to form a pair of fastening ends, and a face fastener is secured to each of a portion of a human body non-contacting face of the supporter body at which the supporter body is not to contact with the human body and a pair of faces of end portions of the fastening ends of the supporter opposite to the human body non-contacting face.

With the construction described above, the supporter can be attached to a portion of the body by wrapping the supporter body around the portion of the body and fastening the face fastener secured to the human body non-contacting face of the supporter body and the other fasteners secured at the fastening ends of the supporter body closely to each other. Further, since a projection of the body can be projected outwardly through the slit formed at the central portion of the supporter body, the supporter can be attached freely to the shoulder, the ankle, a hand root portion, and so on.

BRIEF DESCRIPTION OF THE DRAWINGS

FIG. 5 is a plan view, partly broken, of a supporter according to another embodiment of the present invention showing a human body contacting face of a supporter body of the supporter; and FIGS. 6 and 7 are enlarged cross sectional views taken along lines VI—VI, VII—VII of FIG. 5, respectively.

DETAILED DESCRIPTION OF THE PREFERRED EMBODIMENTS

Figure 1:
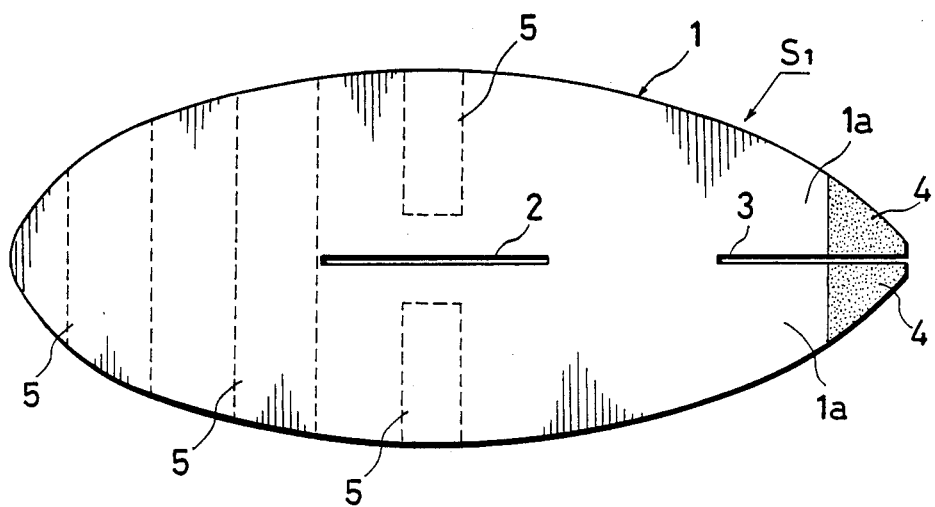
FIG. 1 is a plan view of a supporter according to an embodiment of the present invention showing a human body contacting face of a supporter body of the supporter.
Figure 2:
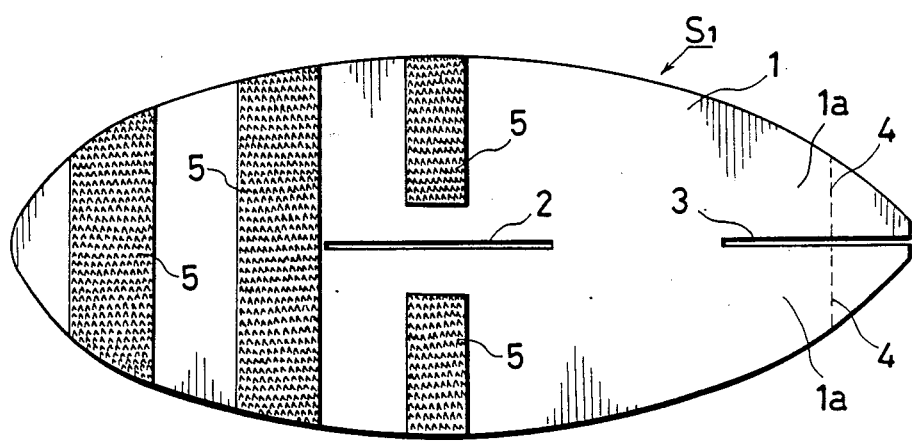
FIG. 2 is a plan view of the supporter of FIG. 1 showing a human body non-contacting face of the supporter body.

Referring first to FIGS. 1 and 2, a supporter $S_1$ may have an elliptical or like overall configuration such as an egg shape or a shape in plan of a Rugby ball and includes a supporter body 1 which has a slit 2 formed in a direction of a longitudinal axis at a central portion thereof. The supporter body 1 further has a longitudinal slit 3 formed at one of opposite longitudinal ends thereof so as to divide the end portion thereof into a pair of fastening ends 1a.

The supporter body 1 has a predetermined strength and stretchability and consists of one or more fabrics which are stretchable in directions of the longitudinal and lateral axes thereof such as knit fabrics with a rib stitch part or stretch fabrics made of strong stretch yarns which are frequently used for ski wear or training pants.

A face fastener 4 is secured to a face of an end portion of each of the fastening ends 1a at which it contacts with the human body (the human body contacting face of the supporter body 1 will be hereinafter referred to simply as rear face) while a plurality of belt-formed face fasteners 5 are secured to the opposite face of the supporter body 1 which does not contact with the human body (the human body non-contacting face of the supporter body 1 will be hereinafter referred to simply as front face). The face fasteners 4 and the other face fasteners 5 can be firmly and closely fastened to each other by facing and pressing them with and against each other. The face fasteners 4, 5 employed here must be such that, where they are closely fastened to each other, they can be readily drawn apart from each other by hand. Such a closely fastening property as described just above may be provided, for example, by a face fastener called magic tape which is constituted such that a face having a large number of inverted V-shaped fibers implanted thereon and another face having implanted thereon a large number of fibers which have inverted L-shaped projections formed at ends thereof may be repetitively fastened closely to and drawn apart from each other.

A stretch bias fabric not shown is sewn along each of an entire outer periphery of the supporter body 1 and peripheral edges of the slits 2, 3 in order to prevent possible fraying of the fabric or fabrics forming the supporter body 1.

Figure 3:
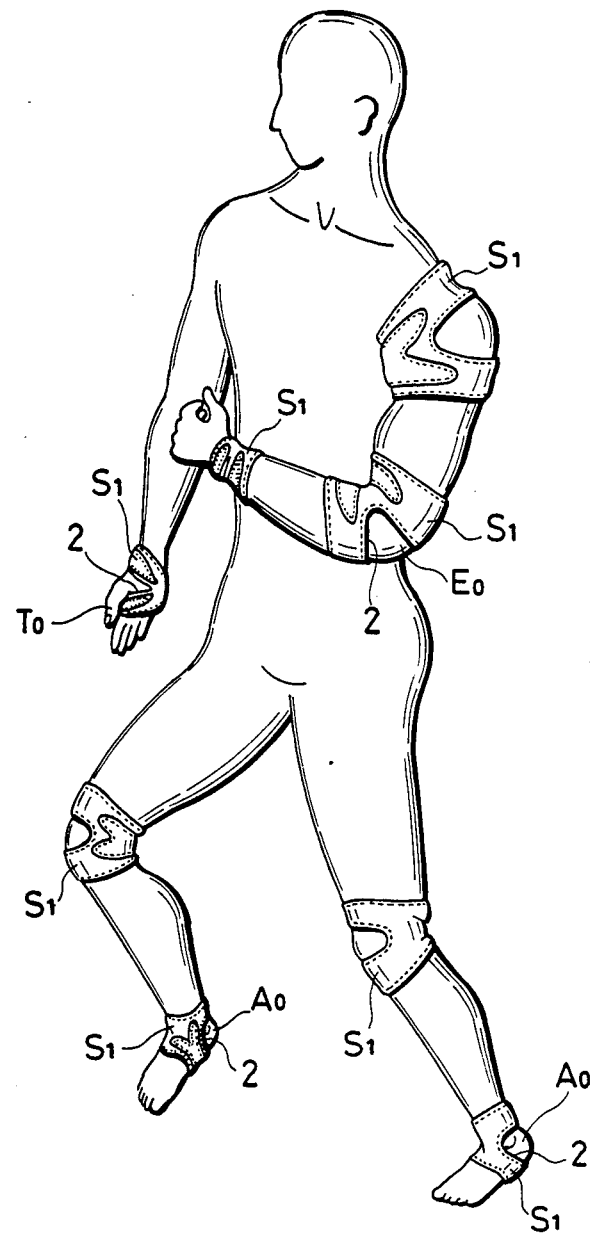
FIG. 3 is an illustration showing different manners of attachment of the supporter of FIG. 1 to various portions of the human body.
Figure 4:
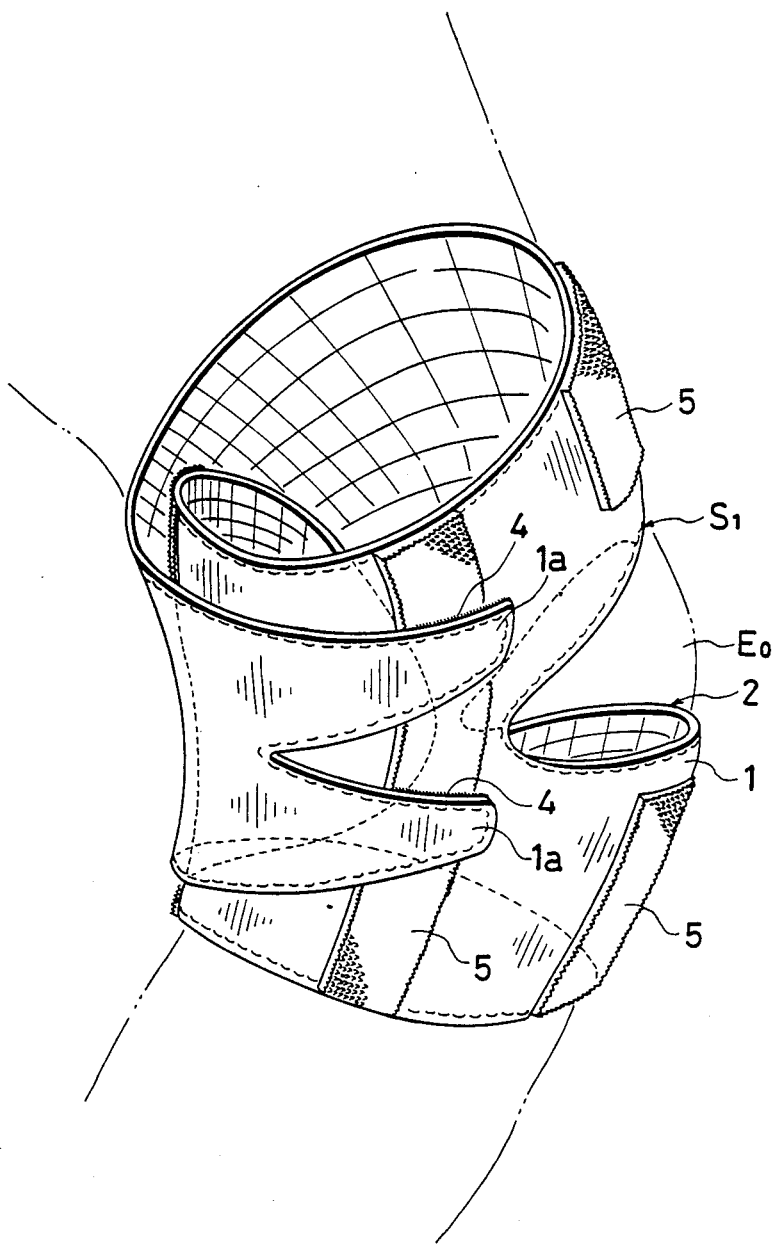
FIG. 4 is a detailed illustration showing a manner of attachment of the supporter of FIG. 1 to the elbow.

The supporter $S_1$ having such a construction as described above can be attached to a given one of portions of the body including the shoulder, the elbow, the wrist, a hand root portion, the knee and the ankle by wrapping the same around the given body portion (refer to FIG. 3). An exemplary attaching process will now be described with reference to FIG. 4 wherein the supporter is to be attached to the elbow. At first, the supporter $S_1$ is held by hand such that the front face of the supporter body 1 may face outside, and is then wrapped around the elbow such that the fastening ends 1a thereof may be wrapped at the last. In this instance, the supporter $S_1$ is positioned such that the slit 2 at the central portion of the supporter body 1 may be located outside the joint $E_0$ of the elbow and is wrapped while applying a tensile force over the entire width of the supporter $S_1$ so that a suitable binding force may be obtained. Since the face fasteners 4 are secured to the rear face portions of the end portions of the fastening ends 1a of the supporter body 1, they can be fixed stably by closely fastening them to casually opposing ones of the face fasteners 5 on the front face of the supporter body 1. Further, since the slit 2 is located outside the elbow joint $E_0$, the elbow joint $E_0$ can be projected outwardly through the slit 2. Accordingly, even where the supporter $S_1$ is attached to the elbow, there is little trouble in flexing the elbow. It is to be noted that when the wrapping end of the supporter $S_1$ is fixed, the pair of fastening ends 1a thereof may cross each other. In this case, a more comfortable feeling of use can be obtained because the substantial width of the supporter $S_1$ is reduced at a portion of the supporter $S_1$ inside the elbow.

Also when the supporter $S_1$ is to be used for another portion of the body than the elbow, it can be attached in a similar manner as illustrated in FIG. 3. For example, when the supporter $S_1$ is to be attached to the ankle, the heel $A_0$ is projected outwardly through the slit 2 of the supporter body 1. On the other hand, when the supporter $S_1$ is to be attached to a hand root portion, the thumb $T_0$ is projected outwardly through the slit 2. Accordingly, the supporter $S_1$ can allow a feeling of stable binding to be obtained without interfering with the exercise of the body. This similarly applies to the shoulder or the knee, but when the supporter $S_1$ is to be attached to a portion of the body such as the wrist, the thigh or the leg which has no special projection thereon, there is no necessity of using the slit 2.

Referring now to FIGS. 5 to 7, there is shown a supporter according to another embodiment of the present invention.

The supporter $S_1$ includes a supporter body 1 which includes an inner fabric 1b and an outer fabric 1c each made of an stretch fabric, an intermediate fabric 10a made of a stretch fabric and interposed between the inner and outer fabrics 1b, 1c, and a plurality of finger-pressing blocks 10 located on the intermediate fabric 10a.

The finger-pressing blocks 10 may be made of, for example, a hard plastics material and have a shape of a frustum of a square pyramid. The finger-pressing blocks 10 are arranged in a regular sequence on portions of the supporter body 1 on opposite sides of a slit 2 at a central portion of the supporter body 1. Consequently, when the supporter $S_1$ is attached to a predetermined portion of the body, the tops thereof will locally press against particular portions of the human body, and accordingly a finger-pressure effect can be obtained by the supporter $S_1$. It is to be noted that in FIGS. 6 and 7 bias fabrics 6 are shown sewn along an entire periphery of the supporter body 1 and along peripheral edges of the slit 2.

It is further to be noted that a plurality of permanent magnets may be arranged in place of the finger-pressing blocks 10. In this instance, a magnetic treating effect can be obtained by the supporter $S_1$ because magnetic lines of force will penetrate the human body.

Here, the shape of the finger-pressing blocks 10 or the permanent magnets located within the supporter body 1 is not limited to that of such a frustum of a square pyramid as shown in FIGS. 5 to 7 but may be any other shape such as a shape of a cylinder, a prism, a frustum of a cone or a disk, and a suitable shape may be selected in accordance with an object which is, for example, to only attain a finger-pressing effect or to only attain a magnetic effect or else to attain both of finger-pressing and magnetic effects. On the other hand, the finger-pressing blocks or the permanent magnets described above may otherwise be applied to a rear surface of the supporter body 1, or else the permanent magnets will sufficiently exhibit a magnetic treating effect even where they are applied to a front surface of the supporter body 1.

According to the supporter $S_1$ describd above, it can not only be used by wrapping it around a portion of the body having any thickness but can allow a projection, which may be present at the body portion to which the supporter $S_1$ is to be attached, to project outwardly through the slit formed therein. Accordingly, the single supporter can be commonly used for any of portions of the human body including the shoulder, the elbow, the wrist, a hand root portion, the knee and the ankle whether or not a projection is present at or around the same. Besides, in attaching the supporter, there is no necessity of operation of drawing up the same from an end of a limb to a portion to which the supporter is to be attached. Accordingly, there is a good effect that an attaching operation is simple and easy.

In addition, since the supporter is used by wrapping it around a portion of the human body to which it is to be attached, there is another good effect that it can be adjusted so as to obtain an optimum binding force.

What is claimed is:

1. A supporter formed from a stretch fabric or fabrics for binding a portion of the human body, characterized in that a supporter body formed in an elliptical shape has a slit formed in a direction of a longitudinal axis at a central portion thereof and is divided at one of opposite longitudinal end portions thereof by another slit extending in the direction of the longitudinal axis of said supporter body to form a pair of fastening ends, and a face fastener is secured to each of a portion of a human body non-contacting face of said supporter body at which said supporter body is not to contact with the human body and a pair of faces of end portions of said fastening ends of said supporter opposite to said human body non-contacting face.

2. A supporter according to claim 1, wherein said supporter body has a plurality of finger-pressing blocks arranged therein.

3. A supporter according to claim 2, wherein said supporter body is composed of two or more overlapping fabrics, and said plurality of finger-pressing blocks are interposed between said fabrics.

4. A supporter according to claim 1 or 2, wherein said supporter has a plurality of permanent magnets arranged therein.

5. A supporter according to claim 4, wherein said supporter body is composed of two or more overlapping fabrics, and said plurality of permanent magnets are interposed between said fabrics.

6. A supporter according to any one of claims 1 to 5, wherein said supporter body has a plurality of face fasteners secured to said human body non-contacting face thereof, said plurality of face fasteners being formed as belts each extending in a direction of a lateral axis of said supporter body and located in a juxtaposed relationship in a direction of the longitudinal axis of said supporter body.

7. A supporter according to any one of claims 1 to 6, wherein a bias fabric is sewn along each of an entire periphery of said supporter body and a peripheral edge of said slit.

* * * * *